US008269956B2

(12) United States Patent
Hashiguchi et al.

(10) Patent No.: US 8,269,956 B2
(45) Date of Patent: Sep. 18, 2012

(54) OPTICAL ELEMENT, REFRACTIVE INDEX SENSOR, REFRACTIVE INDEX SENSOR ARRAY, AND BIOSENSOR

(75) Inventors: Tsuyoshi Hashiguchi, Kanagawa (JP); Hideaki Hirai, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 483 days.

(21) Appl. No.: 12/500,150

(22) Filed: Jul. 9, 2009

(65) Prior Publication Data

US 2010/0014073 A1   Jan. 21, 2010

(30) Foreign Application Priority Data

Jul. 18, 2008 (JP) ................................. 2008-186773

(51) Int. Cl.
*G01N 21/41* (2006.01)
(52) U.S. Cl. ........................................ 356/128; 356/129
(58) Field of Classification Search .................. None
See application file for complete search history.

(56) References Cited

U.S. PATENT DOCUMENTS

| 4,997,278 | A | * | 3/1991 | Finlan et al. | ................... | 356/128 |
| 5,351,127 | A | * | 9/1994 | King et al. | ..................... | 356/445 |
| 7,426,040 | B2 | * | 9/2008 | Kim et al. | ..................... | 356/519 |

FOREIGN PATENT DOCUMENTS

| JP | 5-18890 | 1/1993 |
| JP | 6-58873 | 3/1994 |
| JP | 7-225185 | 8/1995 |
| JP | 2003-121350 | 4/2003 |
| JP | 2005-077287 | 3/2005 |
| JP | 2007-506107 | 3/2007 |
| JP | 2007-156254 | 6/2007 |
| JP | 2007-333893 | 12/2007 |
| JP | 2008-224786 | 9/2008 |
| WO | WO 02/43202 A1 | 5/2002 |
| WO | WO 2005/017570 A2 | 2/2005 |
| WO | WO 2005/017570 A3 | 2/2005 |
| WO | WO 2005/031349 A2 | 4/2005 |

OTHER PUBLICATIONS

World Intellectual Property Organization Publication 2005/017570 A2.*
Wang, Jian et al ("Resonant grating filters as refractive index sensors for chemical and biological detections" Journal of Vacuum science and Technology: Part B, vol. 23, No. 6, Dec. 5, 2005, pp. 3006-3010.*
Jian Jim Wang, et al., "Resonant Grating Filters as Refractive Index Sensors for Chemical and Biological Detections", Journal of Vacuum Science and Technology, vol. 23, No. 6, XP012080297, Dec. 5, 2005, pp. 3006-3010.

(Continued)

*Primary Examiner* — Gregory J Toatley, Jr.
*Assistant Examiner* — Jarreas C Underwood
(74) *Attorney, Agent, or Firm* — Oblon, Spivak, McClelland, Maier & Neustadt, L.L.P.

(57) ABSTRACT

An optical element for resonating and reflecting incident light having a wavelength includes a periodic structure formed of protrusions and recessions. A period of the periodic structure is equal to or less than the wavelength of the incident light. The incident light having the wavelength is resonated and reflected by a resonance caused between the incident light and the protrusions and recessions. Widths of the protrusions are spatially changed.

11 Claims, 16 Drawing Sheets

OTHER PUBLICATIONS

Pradeep Srinivasan, et al., "Fabrication of Variable Effective Refractive Index Artificial Media", Proceedings of SPIE—The International Society for Optical Engineering—Advanced Fabrication Technologies for Micro/Nano Optics and Photonics, Database Accession No. E20081411180498, vol. 6883, XP 002548557, Feb. 6, 2008, 6 pages.

Office Action issued Feb. 28, 2012, in European Patent Application No. 09 251 794.5.

Office Action issued May 15, 2012, in Japanese Patent Appln. No. 2008-186773, filed Jul. 18, 2008, pp. 1-2.

* cited by examiner

OPTICAL ELEMENT, REFRACTIVE INDEX SENSOR, REFRACTIVE INDEX SENSOR ARRAY, AND BIOSENSOR

BACKGROUND OF THE INVENTION

1. Field of the Invention

The present invention generally relates to an optical element that can be used as a resonant filter capable of resonating and reflecting light having a specific wavelength and an optical filter capable of transmitting light having a specific wavelength, to a refractive index sensor and a refractive index sensor array that detect a reaction and a change in a refractive index of a measurement sample by using the optical element, and to a biosensor that checks an antibody reactivity and the like by using the refractive index sensor array. Moreover, the optical element of the present invention can be applied to a polarization sensor that detects a polarization direction of light.

2. Description of the Related Art

In recent years, with the development of biotechnologies, a demand for a biosensor that has high sensitivity and can be manufactured at low cost has been increasing. In this circumstance, a sensor and a device that detect a change in a refractive index have been expected as a sensor for detecting an antigen-antibody complex reaction, a sensor for detecting a change of a component in a specific object or liquid, and a sensor for monitoring a component in blood and urine.

As such a sensor, a sensor using a surface plasmon resonance has been known. Currently, detections are often conducted by labeling a deoxyribo nucleic acid (DNA) or protein with a fluorescence substance and the like and reading the coupled fluorescence substance by a fluorescence microscope or a fluorescence scanner. Since there are advantages in that the preceding step of labeling a fluorescence substance can be omitted and no adverse effect of the preceding step is caused on the DNA, protein, and other substances, a measurement method using the surface plasmon resonance has been actively researched. The surface plasmon resonance is a phenomenon in which surface plasmon waves induced on a metal surface when light is incident to the metal layer is excited by resonating with evanescent waves generated by the incident light. A representative optical structure of a sensor using such a surface plasmon resonance employs total reflection of a prism. To be specific, when light is incident on a prism on which a metal film is deposited by evaporation, evanescent waves generated on a surface of the prism and surface plasmon waves excited on the metal surface resonate with each other. This resonance is called a surface plasmon resonance. An incident angle that causes the surface plasmon resonance changes depending on a refractive index of a sample provided on the metal surface. By utilizing this phenomenon, a change in an angle of the incident light at which the reflected light is reduced has been detected as a change in a refractive index of the surface (see Patent Documents 1 and 2).

In Patent Document 3, the surface plasmon resonance is used as well and has a configuration in which an incident light source, a prism, and a photodetector are fixed. Accordingly, there is no need to adjust a positional relationship among the devices after the sensor is completed. A fixed CCD (Charge Coupled Device) imaging element serves as the photodetector to detect a change in an amount of reflected light of each reflection angle in order to detect a change in the refraction index.

Further, Patent Document 4 discloses a sensing method utilizing a resonant reflection (resonance with reflection) generated when incident light resonates with a structure having a protrusion and a recession, whereby the size of the structure is equal to or less than a wavelength of the incident light. Various modes can be considered to cause this resonant reflection. A simple principle to cause the resonant reflection is shown in FIG. 3 by using a general configuration. A basic structure includes a base material layer 11, a waveguide layer 12 formed of a material with a high refractive index, and a grating layer 13 forming a protrusion-recession periodic structure in which protrusions and recessions are periodically formed. In an area of the grating layer 13, a material part with a high refraction index and a material part with a low refraction index are alternately formed with a predetermined period.

FIG. 4 is a graph showing a transmission factor of light with respect to a wavelength of incident light in the case where a period and a refractive index of the above-described structure are optimized. This shows that incident light resonates and is reflected at only a certain specific wavelength $\lambda 1$ with the structure having a specific period and refractive index in a size equal to or less than a wavelength of the incident light. These components are all formed of a material that is transparent with respect to the incident light. Therefore, most of the incident light is transmitted except that only the above-described condition of the structure having the specific period causes resonant reflection of the incident light.

By using the phenomenon of resonant reflection, a change in a refractive index of the measurement sample can be detected by irradiating an element having a measurement sample with white light and scanning a wavelength of light which resonates and is reflected by a spectroscope. Since labeling with a fluorescence substance and the like is not required in this method either, such problems in that an adverse effect is caused on the substance, the preceding process takes time, and the like can be eliminated. Further, since a high contrast with a high light intensity can be obtained by the resonant reflection, a measurement precision can be enhanced.

[Patent Document 1] Japanese Patent Application Publication No. 5-18890

[Patent Document 2] Japanese Patent Application Publication No. 6-58873

[Patent Document 3] Japanese Patent Application Publication No. 7-225185

[Patent Document 4] Japanese Patent Application Publication No. 2007-506107

However, there have been the following problems in the configurations of the above-described conventional techniques.

By the methods disclosed in Patent Documents 1 and 2, a measurement is performed by utilizing a characteristic of light in that an intensity of reflected light in the total internal reflection changes depending on an incident angle. Therefore, a lens, a prism, and a detector have to be moved at a high positional precision. In order to maintain the positional relationship among these devices, they are required to be fixed by using a member with high rigidity. As a result, an apparatus is enlarged and becomes more expensive.

By the method disclosed in Patent Document 3, the light source, detector, and the like are fixed and a driving part is not provided. Therefore, there is no need of positional adjustment after the setting. Thus, operations can be stabilized. However, since the amount of light of the reflected light at each angle is detected, the CCD used for detection is required to be positioned at a certain distance from the measurement sample. Therefore, this method is not suitable for downsizing and making an apparatus thinner.

By the method disclosed in Patent Document 4, resonant reflection is used for detection, therefore, signals with high contrast can be obtained. However, since a spectroscope is used for this detecting method, it is difficult to downsize the apparatus. Moreover, since only one measurement can be performed with respect to one light source, there are problems in that a process cannot be performed at a higher speed and processes cannot be performed together.

The present invention is made in view of the above circumstances and it is an object of at least one embodiment of the present invention to provide an optical element which causes resonant reflection (resonance with reflection) of light having a specific wavelength by utilizing resonant reflection caused by a periodic structure formed of fine protrusions and recessions in a size equal to or less than a wavelength of incident light. Further, it is an object of at least one embodiment of the present invention to provide a refractive index sensor and a refractive index sensor array which has no moving part; can perform a stable measurement at a high precision; can make an element smaller and thinner; and can make a process speed higher by employing the optical element, and to provide a biosensor that checks an antibody reactivity and the like by using the refractive index sensor array.

To achieve the above objects, following measures are employed in the present invention.

SUMMARY OF THE INVENTION

According to one aspect of the present invention, an optical element for resonating and reflecting incident light having a wavelength includes a periodic structure formed of protrusions and recessions. A period of the periodic structure is equal to or less than the wavelength of the incident light. The incident light having the wavelength is resonated and reflected by a resonance caused between the incident light and the protrusions and recessions. Widths of the protrusions are spatially changed.

According to another aspect of the present invention, a refractive index sensor includes an optical element for resonating and reflecting incident light having a wavelength. The optical element includes a periodic structure formed of protrusions and recessions. A period of the periodic structure is equal to or less than the wavelength of the incident light. The incident light having the wavelength is resonated and reflected by a resonance caused between the incident light and the protrusions and recessions. Widths of the protrusions are spatially changed. The refractive index sensor further includes a photodetector configured to detect a position on the optical element where the incident light is reflected. The position on the optical element changes in accordance with a refractive index of a sample provided on the optical element.

According to another aspect of the present invention, a refractive index sensor array includes a refractive index sensor including an optical element for resonating and reflecting incident light having a wavelength. The optical element includes a periodic structure formed of protrusions and recessions. A period of the periodic structure is equal to or less than the wavelength of the incident light. The incident light having the wavelength is resonated and reflected by a resonance caused between the incident light and the protrusions and recessions. Widths of the protrusions are spatially changed. The refractive index sensor further includes a photodetector configured to detect a position on the optical element where the incident light is reflected. The position on the optical element changes in accordance with a refractive index of a sample provided on the optical element. The refractive index sensor is arranged in a one-dimensional or two-dimensional array.

DETAILED DESCRIPTION OF THE PREFERRED EMBODIMENTS

Figure 1:
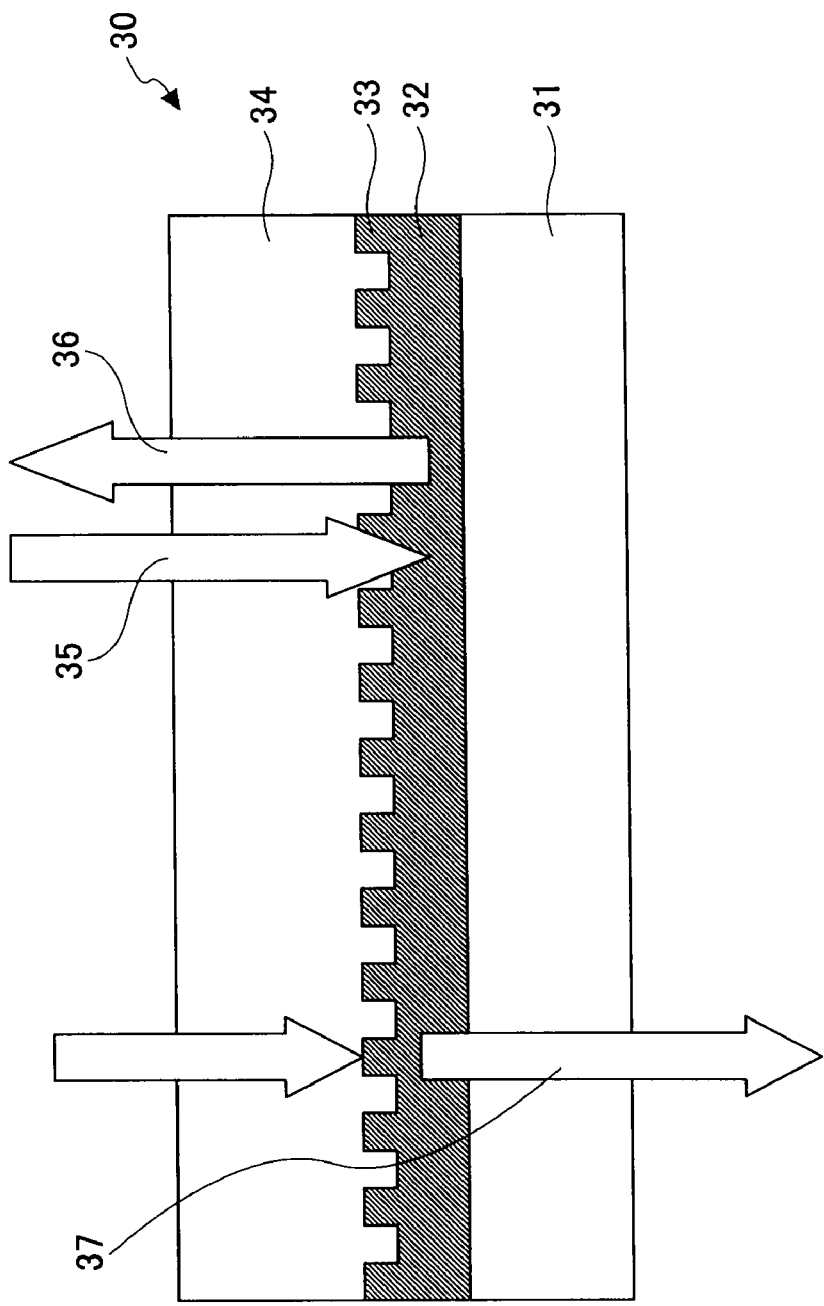
FIG. 1 illustrates a cross-sectional diagram showing a representative structure example of an optical element which causes a resonant reflection as an embodiment of the present invention.

Hereinafter, structures, operations, and effects of the present invention are described in detail.

An optical element of an embodiment of the present invention has a structure in which a structure width (width of protrusions) of a periodic structure formed of protrusions and recessions is spatially changed. More specifically, the optical element of an embodiment of the present invention has a structure in which a structure width is spatially changed in a state where a period of the periodic structure is constant, or a structure in which the structure width is spatially changed in a state where the periodic structure has a constant refractive index. The optical element with the above structure transmits or reflects light having a specific wavelength by utilizing resonant reflection caused by the fine protrusions and recessions in a size equal to or less than a wavelength of incident light.

A resonant filter formed of the optical element of an embodiment of the present invention resonates and reflects incident light having a specific wavelength by utilizing the resonance caused between the incident light and the periodic structure formed of the fine protrusions and recessions in a size equal to or less than the wavelength of the incident light.

Further, an optical filter formed of the optical element of an embodiment of the present invention transmits light having a specific wavelength by utilizing the resonance caused between the incident light and the periodic structure formed of the fine protrusions and recessions in a size equal to or less than the wavelength of the incident light.

A refractive index sensor of an embodiment of the present invention includes an optical element which resonates and reflects incident light having a specific wavelength by utilizing resonance caused between the incident light and a periodic structure having fine protrusions and recessions in a size equal to or less than a wavelength of the incident light, and a photodetector which detects light transmitted or reflected by the optical element. By spatially changing a structure width of the periodic structure formed of the fine protrusions and recessions while maintaining a constant period (or a constant refractive index), a refractive index of a part (measurement sample) around the protrusions and recessions is detected by a position of the structure width where resonant reflection of the incident light occurs.

Here, as a specific embodiment mode of the present invention, a description is made of an example where the optical element is used as a resonant filter.

A resonant reflection wavelength, which is a wavelength at which resonant reflection occurs, of the resonant filter formed of the optical element of an embodiment of the present invention is determined depending on a period (pitch) of a fine periodic structure, a structure width and a refractive index of the periodic structure, a refractive index of a part (measurement sample) around the periodic structure, and the like. Therefore, by changing the structure width of the periodic structure while setting the period (pitch) and the refractive index of the periodic structure constant, that is, by changing a ratio (fill factor) of the structure width with respect to the period, a fine change of a refractive index of a part (measurement sample) around the periodic structure can be detected as a change in a wavelength of light which resonates and is reflected. That is, when incident light has a single wavelength, a minute change in the refractive index caused around the periodic structure can be detected by a value of a fill factor of the periodic structure. Therefore, by forming a structure in which a fill factor of a periodic structure formed of fine protrusions and recessions is spatially changed, a minute change of a refractive index caused around the periodic structure can be detected as a change of a spatial position corresponding to the fill factor.

By manufacturing a resonant filter with such a structure, a change in a refractive index caused around the periodic structure can be detected without requiring a spectroscopy function. Thus, it is very advantageous in downsizing and simplifying elements. Moreover, since a change of the fill factor corresponds to a minute change of the refractive index caused around the periodic structure, sensitivity of the refractive index sensor can be considerably increased.

By forming the photodetector by using plural light receiving elements and arranging the light receiving elements in an array corresponding to the changes in the fill factor, a change in the refractive index can be detected in real time as a change of a position where resonant reflection occurs.

As the photodetector, a linear CCD or a linear CMOS (Complementary Metal-Oxide Semiconductor) sensor, and the like can be used.

Further, by serially stacking the photodetector and a measurement sample including the periodic structure, a thickness of the sensor can be considerably reduced.

Furthermore, by arranging the refractive index sensor in a one-dimensional or two-dimensional array, detections and processing of plural changes in refractive index can be performed together by using one light source.

Here, a basic structure of a refractive index sensor, in which the optical element of an embodiment of the present invention is used as a resonant filter and combined with a photodetector, is described with reference to the drawings.

FIG. 1 shows a cross-sectional view of a representative structure of an optical element which causes resonant reflection with respect to incident light.

An optical element (resonant filter) 30 has a base material layer 31, a waveguide layer 32, and a grating layer 33. The grating layer 33 has a periodic structure formed of fine protrusions and recessions. A measurement sample layer 34 is formed over the grating layer 33. In the structure shown in FIG. 1, incident light 35 is incident from the measurement sample layer side. With this structure, reflected light 36 can be obtained at a part having a resonant reflection condition with respect to the incident light, while most of the incident light becomes transmitted light 37 at parts having other conditions.

Figure 2:
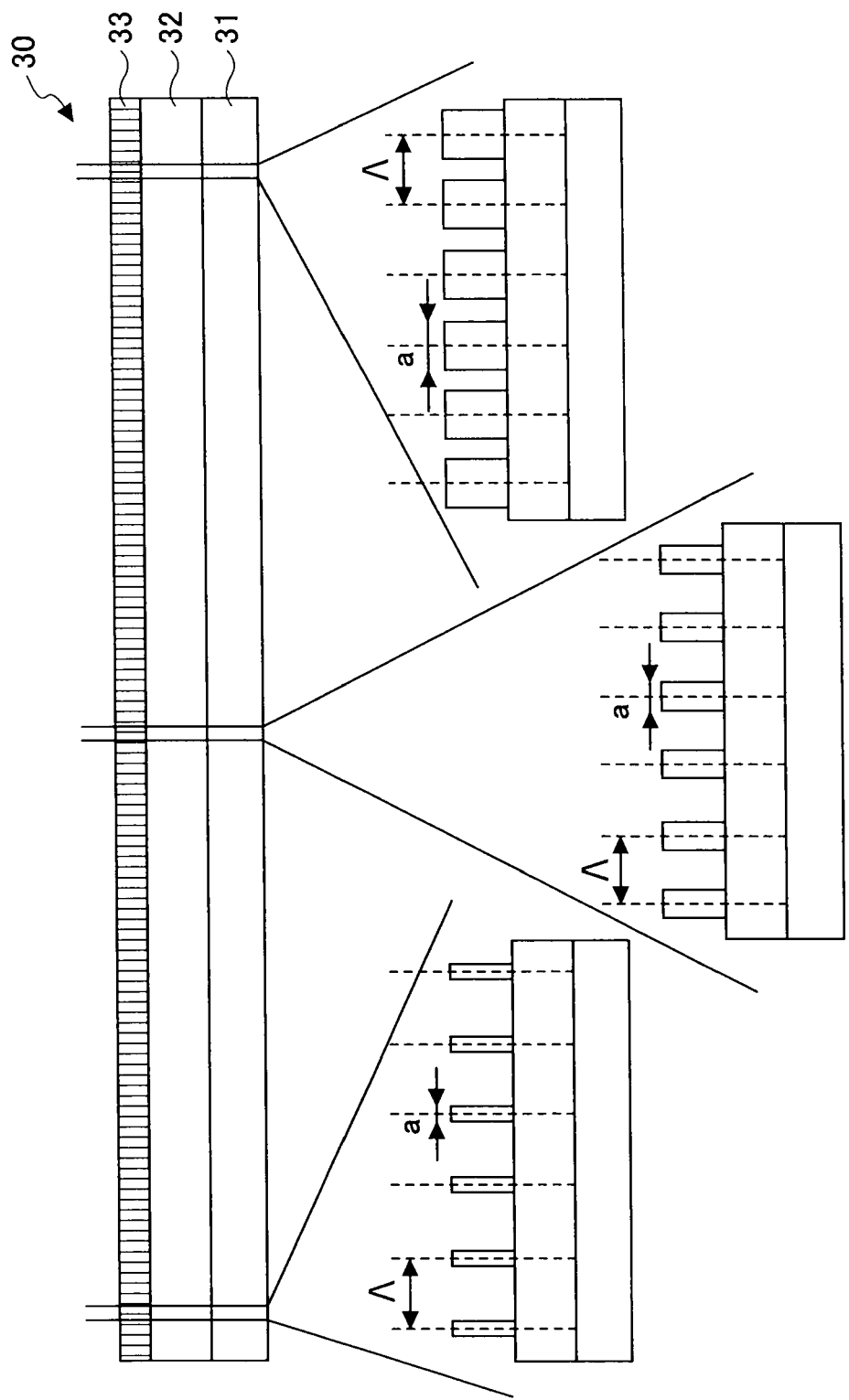
FIG. 2 illustrates a diagram showing a configuration example of a resonant filter structure in a refractive index sensor of the present invention.
Figure 3:
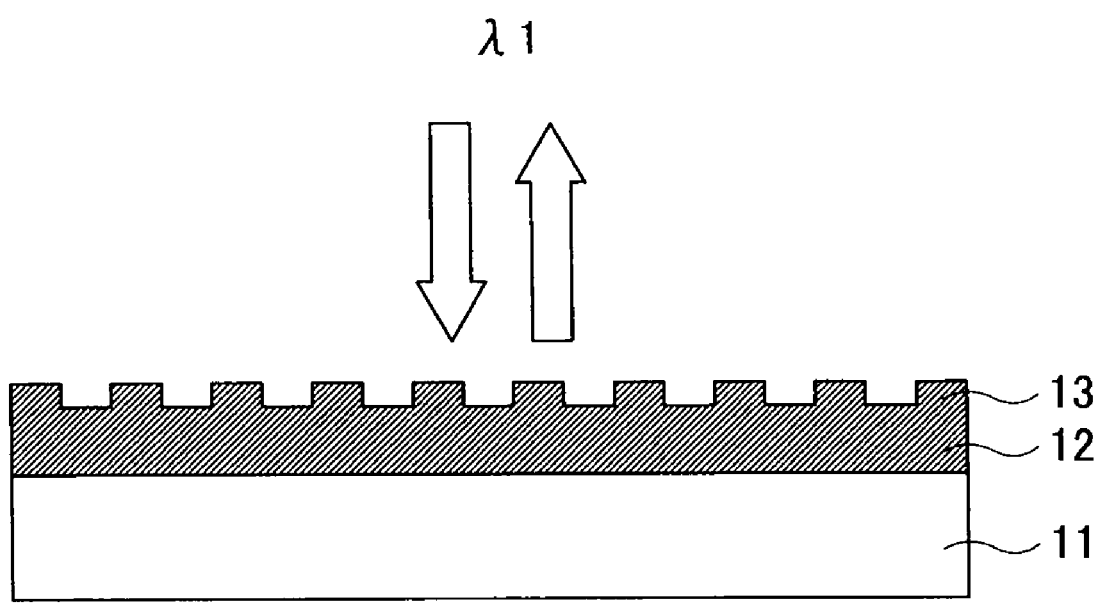
FIG. 3 illustrates a diagram showing a configuration example of an optical element having a resonant structure related to the present invention.
Figure 4:
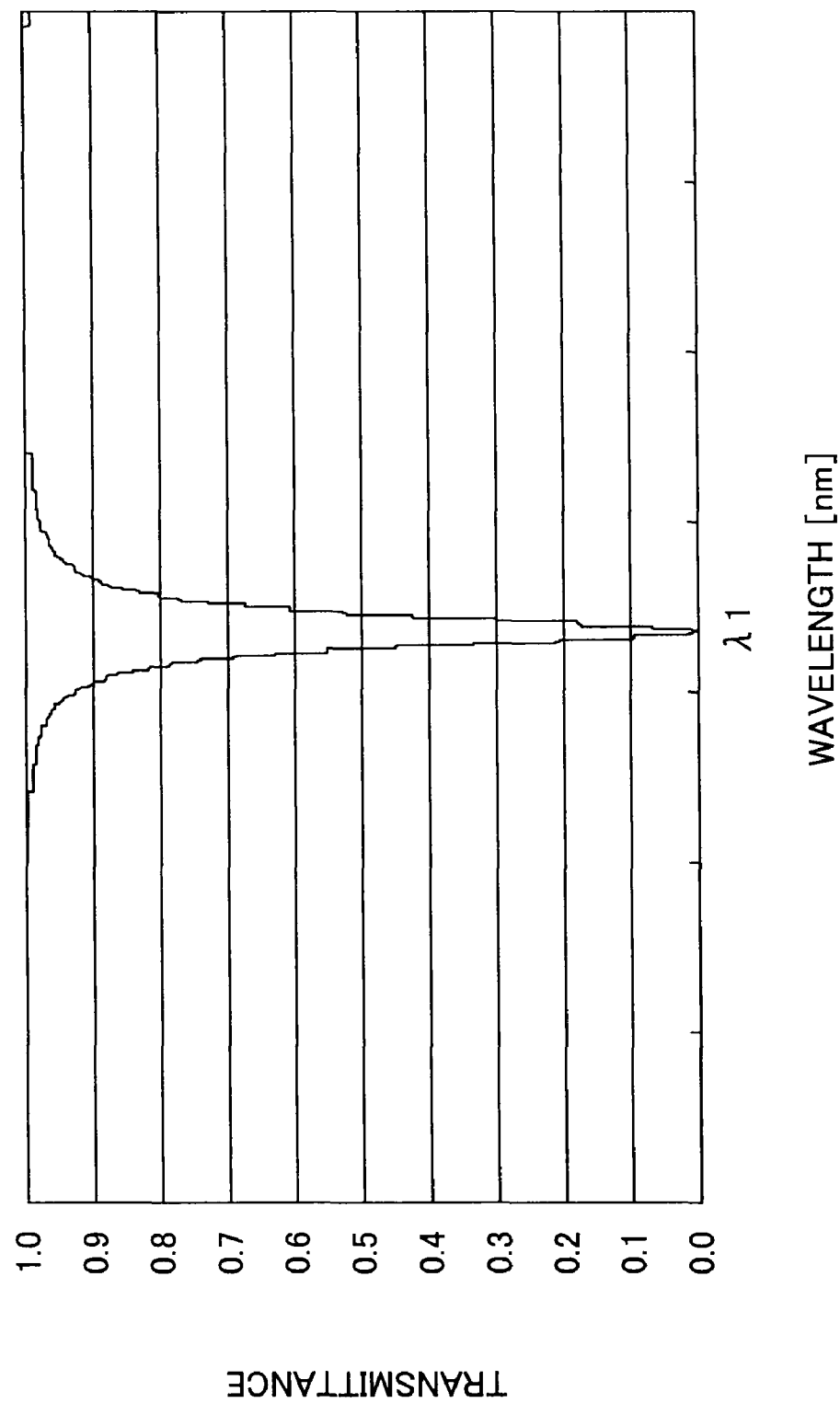
FIG. 4 is a graph showing transmittance of the resonant structure shown in FIG. 3.
Figure 5:
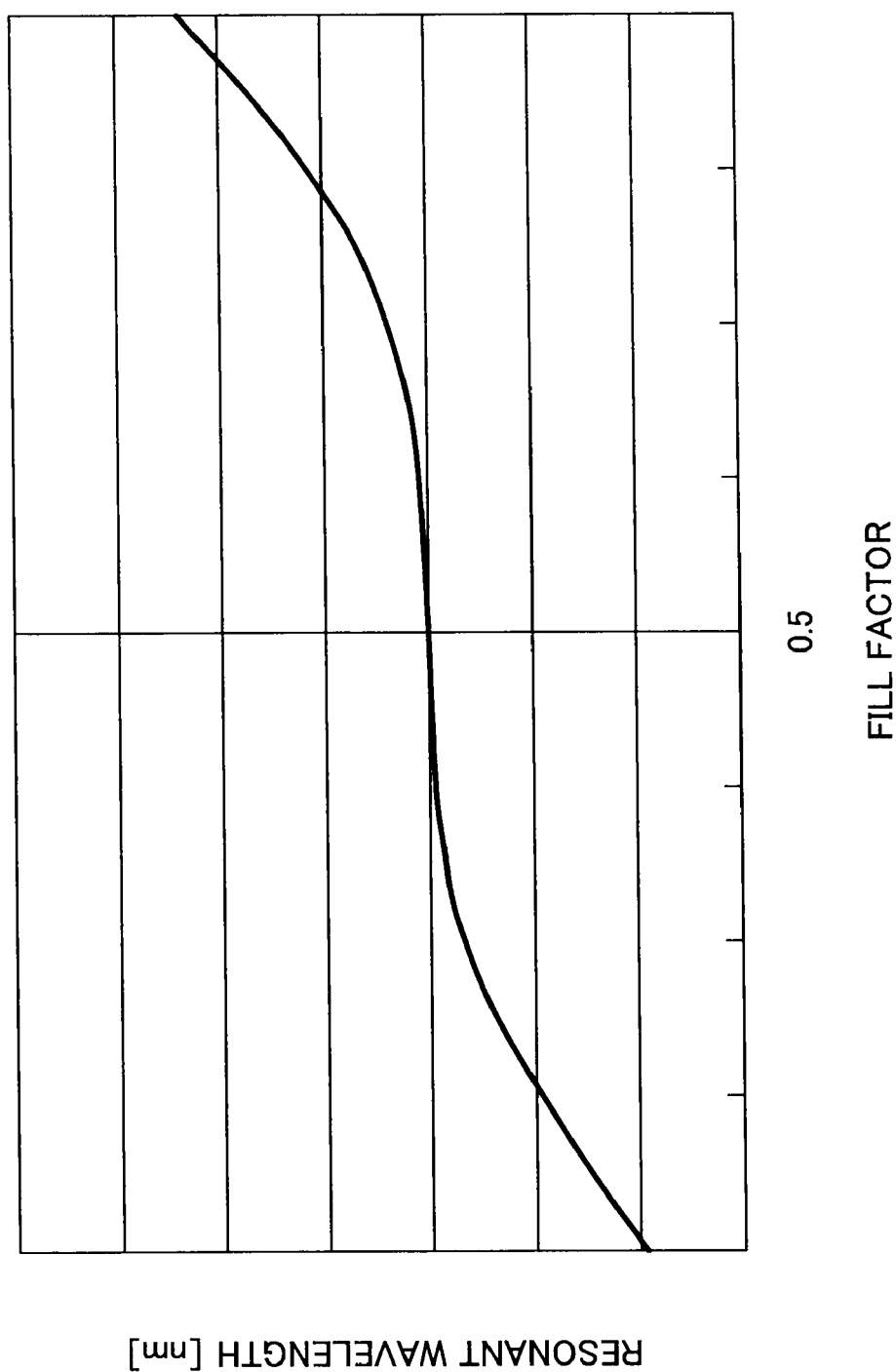
FIG. 5 is a graph showing a change of a resonant wavelength in the case where a fill factor of a grating layer in the resonant filter shown in FIG. 2 is changed.

FIG. 2 shows a structure of the resonant filter according to an embodiment of the present invention. In the entire structure, a structure period "$\Lambda$" of the grating layer 33 is constant, while a structure width (width of a protrusion) "a" gradually changes spatially. That is, a fill factor $F=a/\Lambda$ gradually changes depending on the position. Here, only the fill factor changes depending on the position, while the period $\Lambda$ and refractive indexes of the grating layer, and the waveguide layer are constant. FIG. 5 is a graph showing a change of a resonant wavelength caused when the fill factor is changed. When the fill factor is about 0.5, there is little change in the resonant wavelength. As the fill factor moves away from 0.5, a change amount in the resonant wavelength becomes larger. That is, by forming a periodic structure with fine protrusions and recessions in which a fill factor F spatially changes, an element in which a resonant wavelength (wavelength at which incident light resonates) spatially changes corresponding to the change of the fill factor F can be manufactured.

Figure 6:
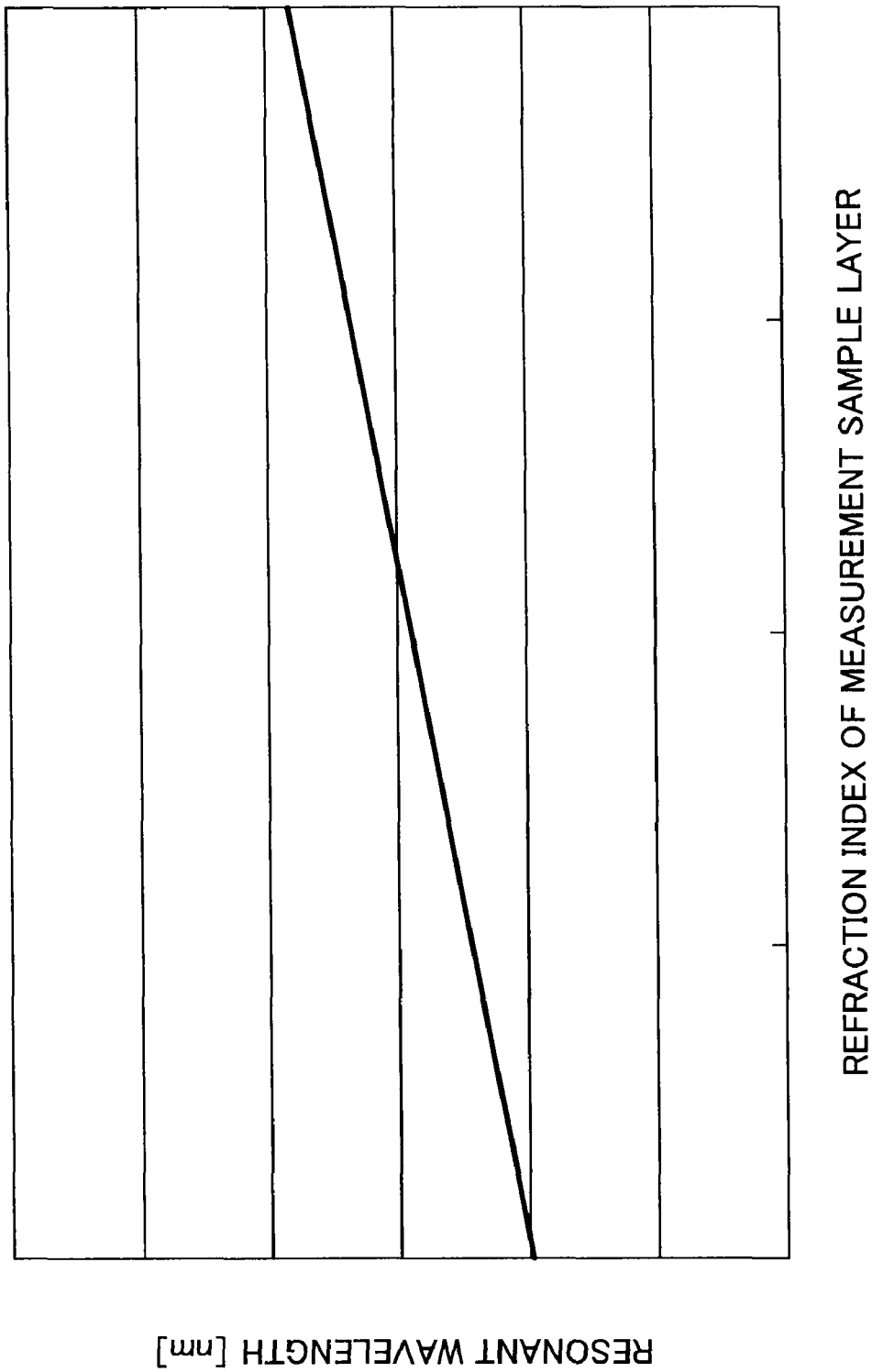
FIG. 6 is a graph showing a change in a resonant wavelength in the case where a refractive index of a measurement sample layer on the optical element (resonant filter) in FIG. 1 is changed.

Next, when a refractive index of the measurement sample layer 34 in FIG. 1 is changed, the resonant wavelength changes as shown in a graph of FIG. 6. Here, the refractive index of the measurement sample layer 34 and the resonant wavelength change in proportion. That is, this graph shows that when the refractive index of the measurement sample layer 34 changes, the resonant wavelength changes accordingly.

In the case where a wavelength λ1 of incident light to the element is fixed, the fill factor with which the resonant reflection is caused changes when the refractive index of the measurement sample layer changes, according to relationships in changes between the fill factor and the resonant wavelength, and between the refractive index of the measurement sample layer and the resonant wavelength. Accordingly, by manufacturing a structure of which the fill factor is spatially changed and irradiating the structure with light having the specific wavelength λ1, a minute change in the refractive index of the measurement sample layer can be detected as a position where a resonant reflection occurs.

Figure 7:
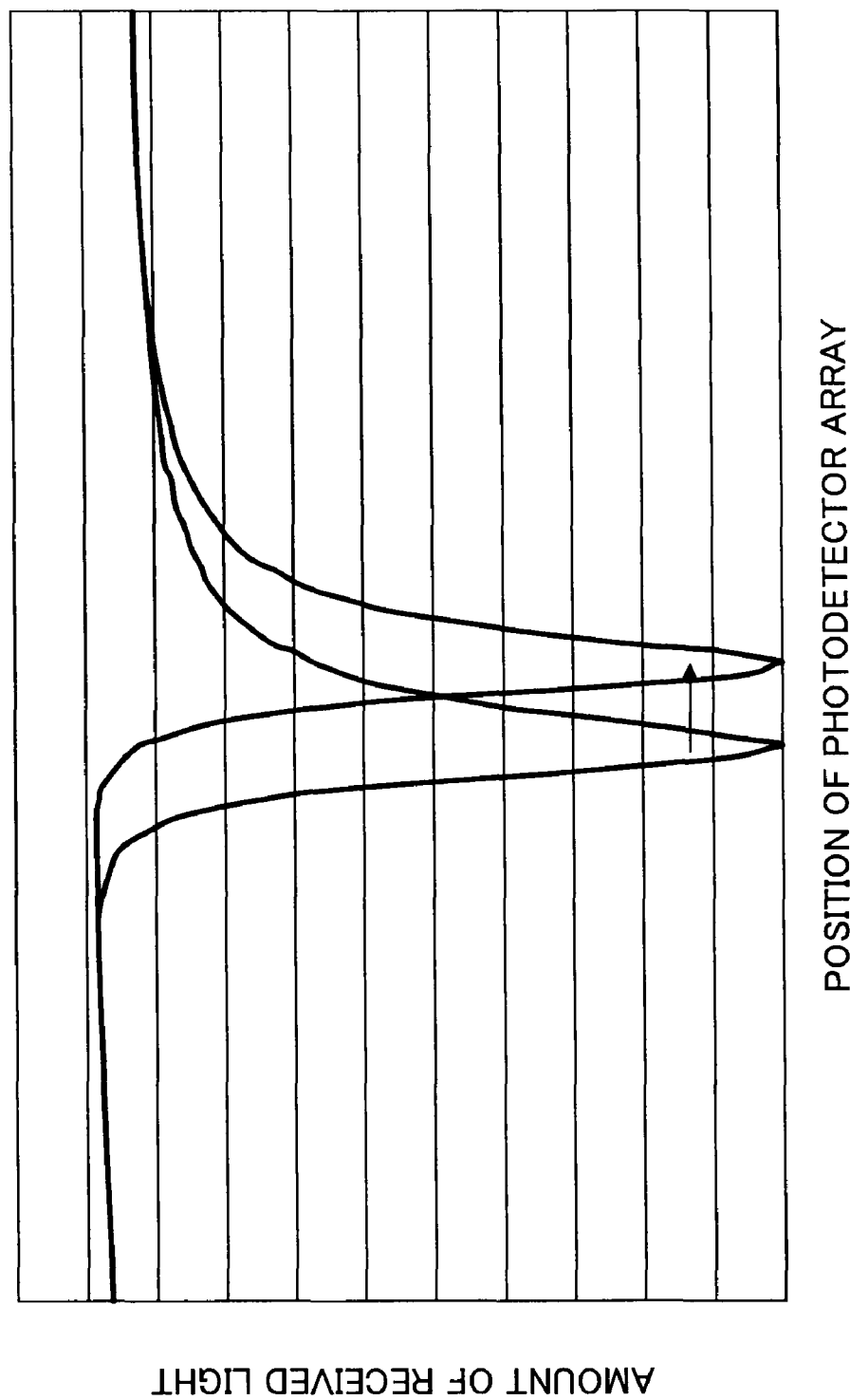
FIG. 7 is a graph showing a change in an amount of received light depending on a position, which is detected by a photodetector array of a refractive index sensor of the present invention.

Here, in the refractive index sensor of an embodiment of the present invention, by arranging the photodetectors formed of CCDs or CMOS sensors in an array corresponding to the spatial fill factor of the resonant filter, signals are obtained by the photodetector array as shown in FIG. 7. Changes in the refractive index of the measurement sample layer can be detected in real time all at the same time.

Further, by stacking the photodetectors formed of CCDs or CMOS sensors with the resonant filter which causes a resonant reflection, a smaller and thinner refractive index sensor can be manufactured.

Since a resonant wavelength of the resonant filter also changes depending on an angle of the incident light, it is easy to adjust the resonant wavelength by minutely adjusting an angle of the refractive index sensor.

Embodiment 1

A more specific embodiment of the present invention is described with reference to the drawings.

A basic structure of a resonant filter in a refractive index sensor of the embodiment of the present invention includes, as shown in FIG. 1, the waveguide layer 32 formed over the base material layer 31, and the grating layer 33 having a structure with periodic protrusions and recessions (hereinafter also referred to as a periodic protrusion-recession structure), which causes a resonant reflection with respect to incident light, is formed over the waveguide layer 32. Over the grating layer 33, the measurement sample layer 34 is formed so as to cover the fine periodic structure. In order to enable a resonant reflection of the incident light, there needs to be a difference in refractive indexes between a material of the grating layer 33 of the periodic protrusion-recession structure and a material of the measurement sample layer 34 filled between the protrusions and recessions of the grating layer 33.

In this embodiment, the base material layer 31 is formed of quartz glass, while the waveguide layer 32 and the grating layer 33 thereover are formed of $TiO_2$ with a high refractive index. The measurement sample layer 34 formed thereover is formed of a mixed solution of pure water and ethanol.

Figure 8:
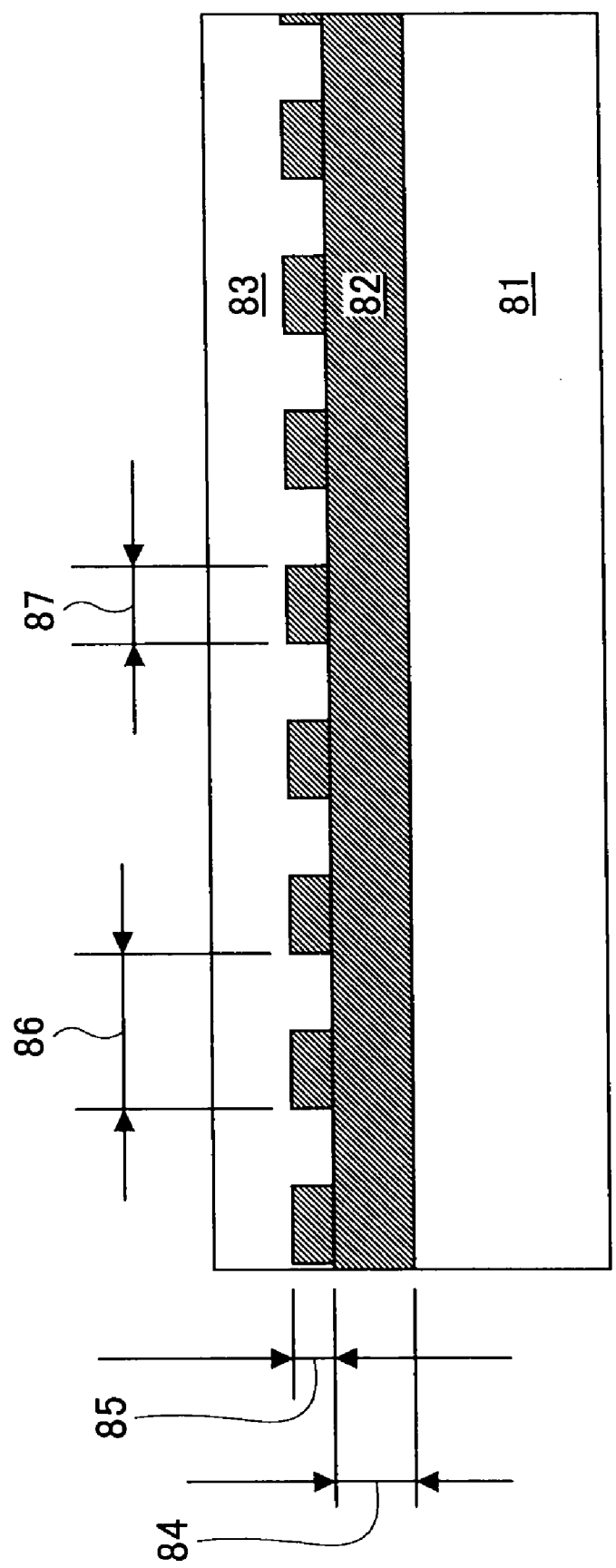
FIG. 8 illustrates a cross-sectional diagram of a structure of an optical element (resonant filter) of the present invention to cause a resonant reflection.

When light having a wavelength of 780 nm is used as the incident light, a refractive index of the base material layer 31 is 1.45, a refractive index of $TiO_2$ is 2.20, and a refractive index of the measurement sample layer 34 is 1.36 when ethanol is employed. In the case where an angle between a polarization direction of the incident light and a direction of the fine periodic structure is 90°, the incident light causes resonant reflection when, in FIG. 8, a period (pitch) 86 is 400 nm, a height 85 of the grating layer is 30 nm, and a thickness 84 of a high refractive index layer 82 of a part where the protrusion or recession is not formed is 20 nm. Here, the fill factor was changed from 0.5 to 0.75, that is, the structure width 87 was spatially changed from 200 to 300 nm. Areas having the fill factors of 0.5 or higher were employed because the fine protrusion-recession structure can be manufactured more stably by changing the wide structure widths.

Figure 9:
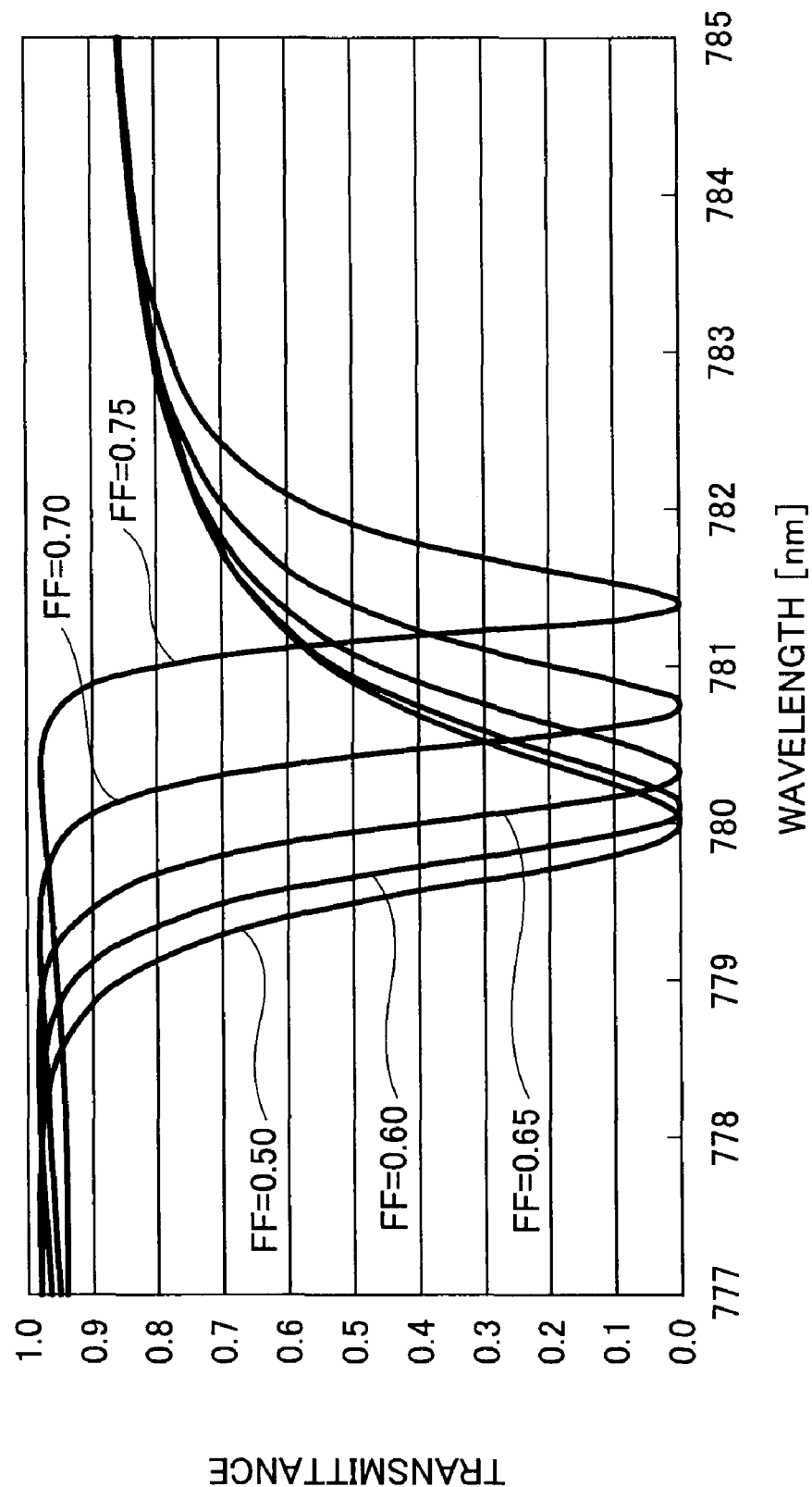
FIG. 9 is a graph showing a change in transmittance with respect to a wavelength in the case where a fill factor of an optical element (resonant filter) of the present invention is changed.
Figure 10:
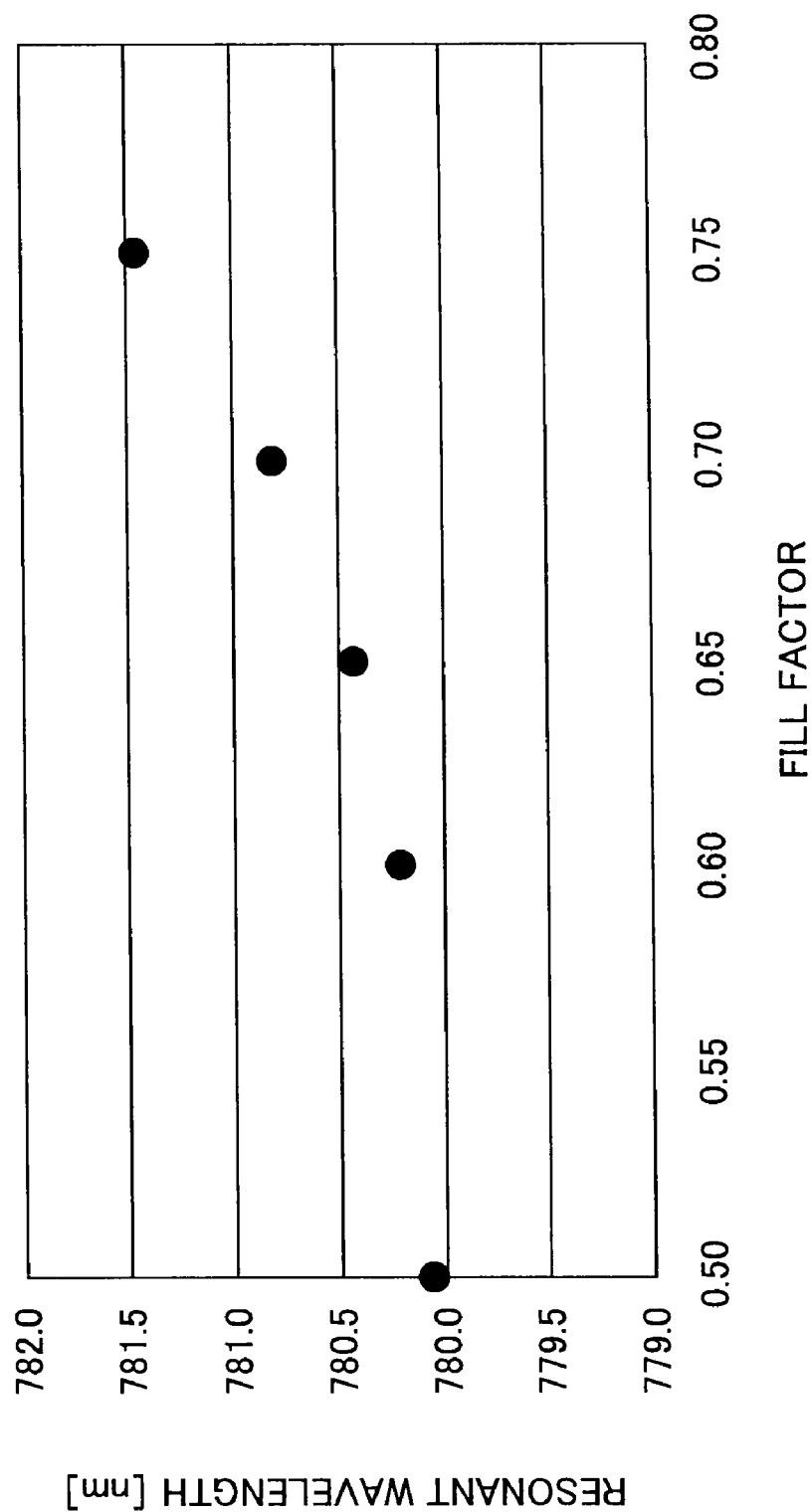
FIG. 10 is a graph showing a change in resonant wavelength with respect to a fill factor of an optical element (resonant filter) of the present invention.
Figure 11:
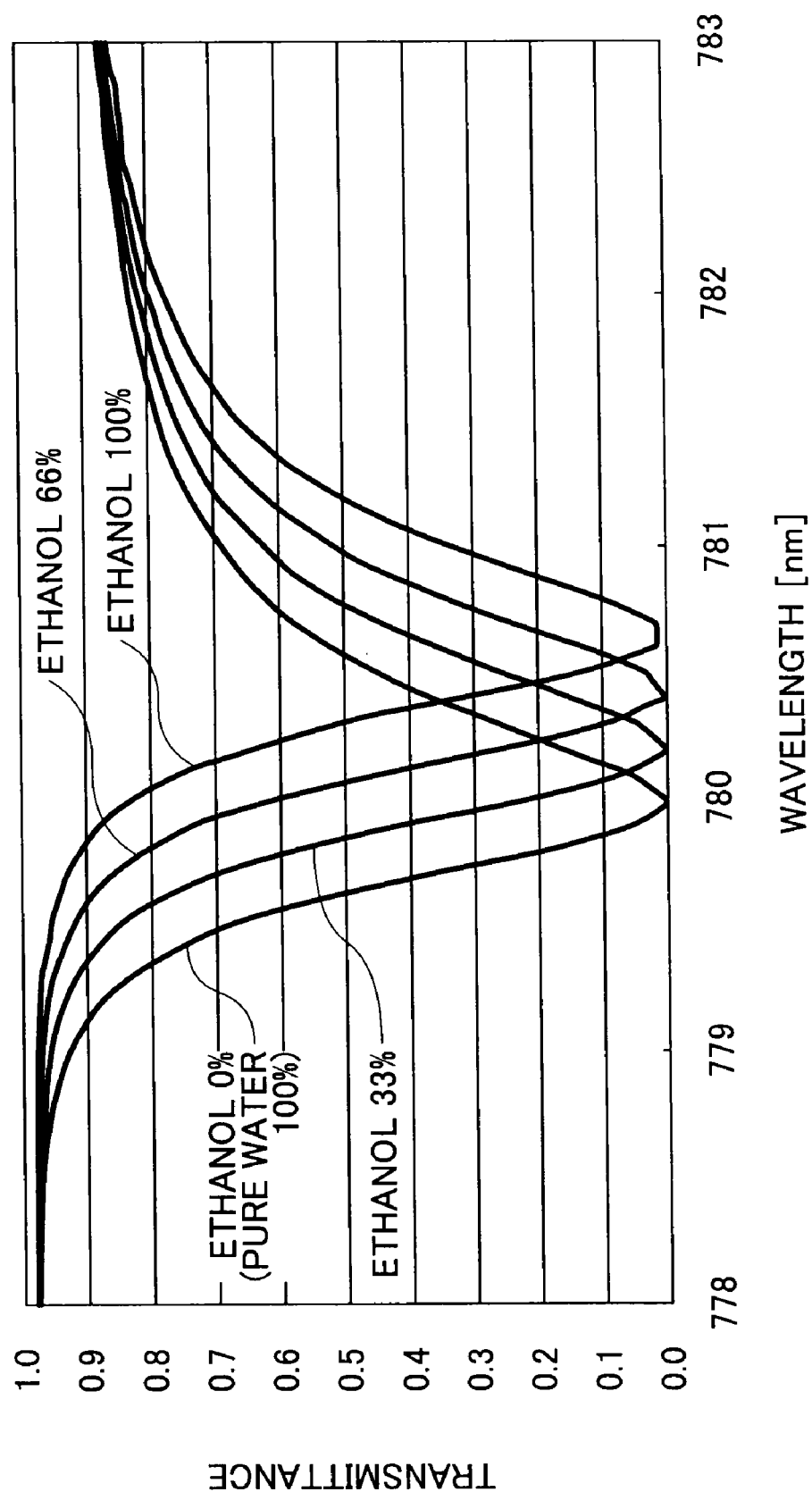
FIG. 11 is a graph showing a change in transmittance with respect to a wavelength in the case where a refractive index of a measurement sample layer is changed.

FIGS. 9 and 10 are a graph showing transmittance of the resonant filter and a graph showing a change in the resonant wavelength, respectively, in the case where ethanol was actually used as the material of the measurement sample and the fill factor was actually changed from 0.5 to 0.75. FIG. 11 is a graph showing transmittance of the resonant filter in the case where the fill factor was set at 0.5 and a mixed solution of pure water and ethanol was used as the material of the measurement sample. A refractive index of 1.33 to 1.36 can be detected as a change of the resonant wavelength.

When a resonant filter having a fill factor changed from 0.5 to 0.75 without changing a pitch of 400 nm was used, an amount of transmitted light is reduced in an area with the resonant condition, while almost all the light is transmitted through the resonant filter in an area further from the area with the resonant condition, depending on a position of the fill factor. Accordingly, a change in the refractive index of the measurement sample can be converted to a change in a position of the fill factor which causes the resonance. Moreover, by this method, there is quite a high contrast between transmittance and reflection of light having a wavelength in the vicinity of the resonant wavelength. Therefore, a change in the refractive index can be detected with high sensitivity.

Embodiment 2

Next, a second embodiment of a refractive index sensor of the present invention is described.

A basic structure of the resonant filter used in the refractive index sensor is the same as that of embodiment 1.

Figure 12A:
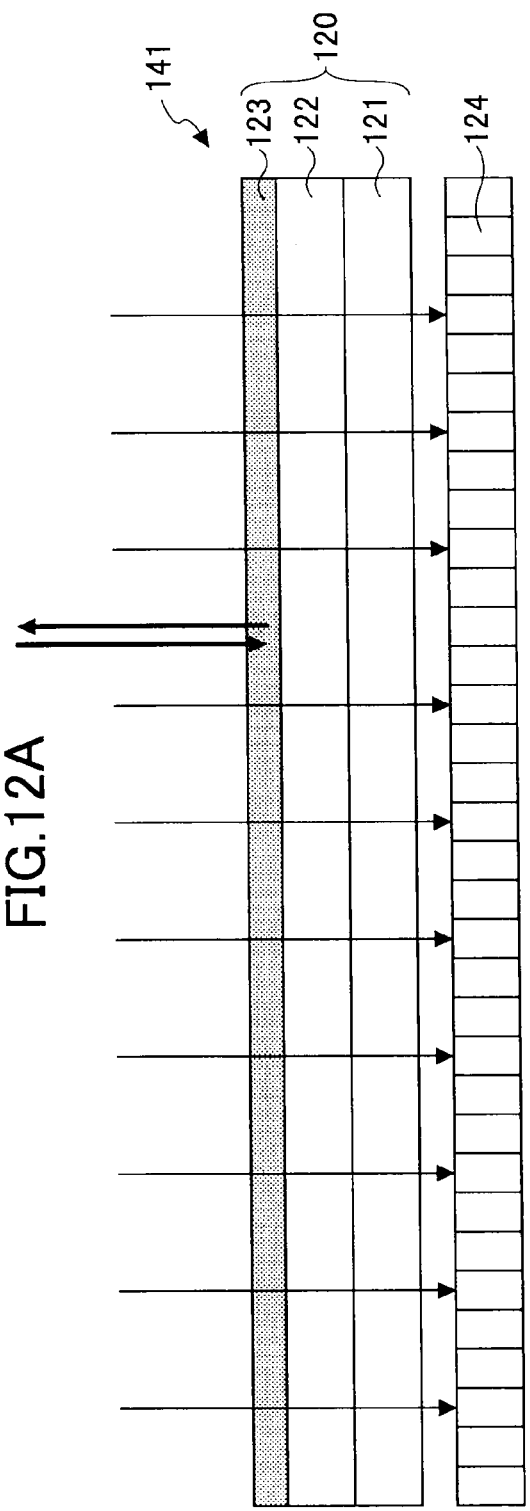
FIG. 12A illustrates a diagram showing an embodiment of a refractive index sensor of the present invention and FIG. 12B is a diagram showing a positional relationship between a resonant filter of a refractive index sensor and a photodetector, and obtained signals.
Figure 12B:
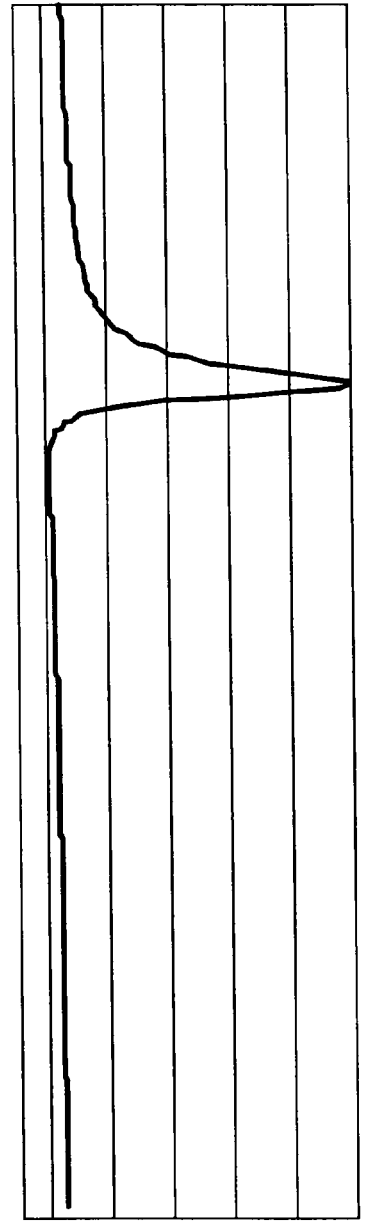
Figure 13:
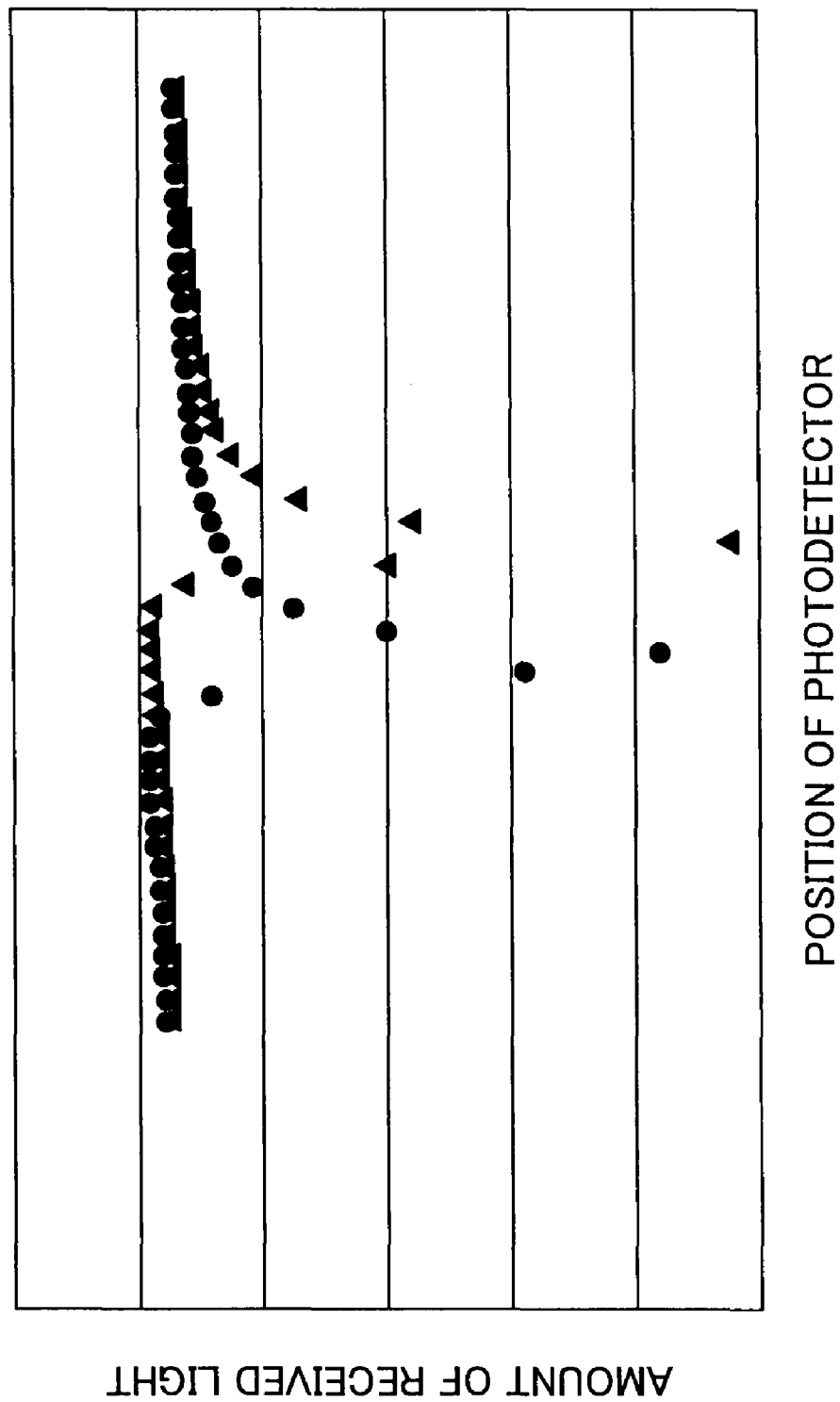
FIG. 13 is a graph showing an example of signals detected by a photodetector of a refractive index sensor of the present invention.

FIG. 12A shows a basic structure of the refractive index sensor. A resonant filter 120 includes a base layer 121, a waveguide layer 122, and a grating layer 123 having protrusions and recessions whose fill factor is spatially changed as described in embodiment 1. A light receiving element array formed of plural light receiving elements, a linear CCD, or a linear CMOS sensor is provided as a photodetector 124 so as to correspond to the changes of the fill factor. In this embodiment, a linear CCD with a pixel size of 20 μm was employed as an example, and the fill factor of the grating layer 123 was formed so that a structure width changes per 20 μm corresponding to the pixel size of the CCD. Further, the structure width was set to change by an amount of 10 nm. With such a structure, a position where a resonant reflection occurs can be detected as shown in FIG. 13. Therefore, a change in the refractive index can be measured in real time at a high speed.

Here, one pixel of the linear CCD serving as the photodetector 124 does not necessarily have to correspond to a condition of the changes of the fill factor. It is only required that the CCD has as many pixels as the changes of the fill factor or more. Further, the fill factor is not required to change in stages, but may gradually change. If the resolution is required to be increased, the amount of change of the structure width may be reduced.

It is structurally preferable that the photodetector 124 and the resonant filter 120 having the spatially changing fill factor be stacked as shown in FIG. 12A. Accordingly, a very simple sensor for detecting a resonant reflection with high precision can be formed. In addition to the aspect that the optical element can be formed smaller and thinner, alignment between the resonant filter 120 and the photodetector 124 is facilitated; therefore, it is advantageous to form a transmitting type structure.

Embodiment 3

An embodiment of a refractive index sensor array of the present invention is described below.

Figure 14:
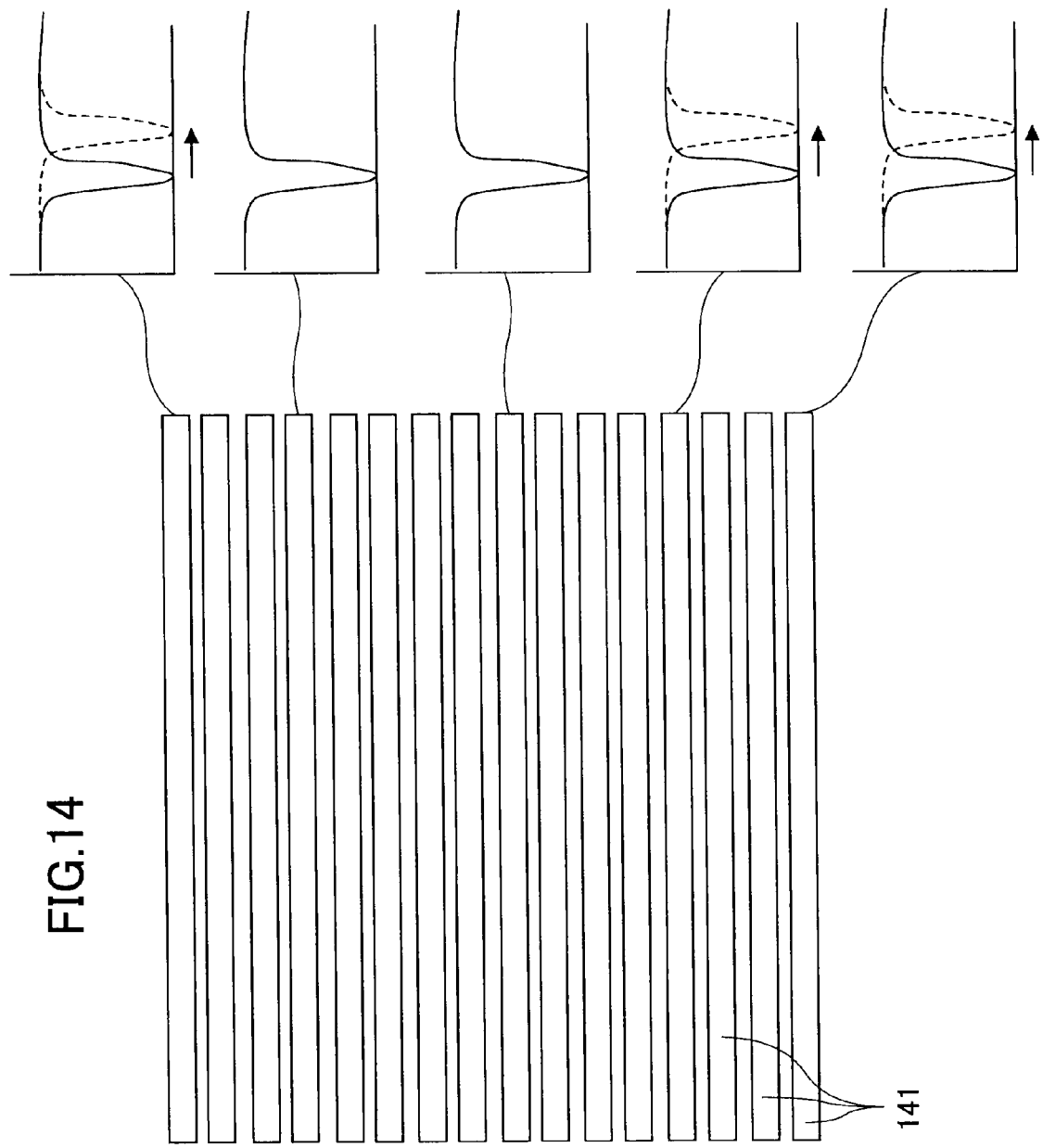
FIG. 14 illustrates a diagram showing an embodiment of a refractive index sensor array of the present invention, showing a configuration example of refractive index sensors arranged in an array and examples of detected signals.

As shown in FIG. 14, refractive index sensors 141 formed by stacking the photodetector 124 and the resonant filter 120 having a changing fill factor, which are described in embodiment 2, are arranged in an array. In FIG. 14, the refractive index sensor 141 has a fill factor changing in a lateral direction. A plurality of the refractive index sensors 141 is arranged in a vertical direction to form a one-dimensional array. When incident light with a single wavelength is uniformly emitted to the array in this state, reactions and changes of the refractive index sensors 141 can be detected at the same time.

Here, the refractive index sensor array can be used as a biosensor as one of application examples. The refractive index sensor array can be used as the biosensor, for example, by fixing different probe DNAs on surfaces of the refractive index sensors of the refractive index sensor array. When a sample including a target DNA is applied over an entire surface of the refractive index sensor array, a change in a refractive index can be detected in only a sensor part where the probe DNA and the target DNA are hybridized. In this manner, vital reaction checks of DNA and protein can be performed in parallel with a high precision.

Embodiment 4

An outline of a manufacturing method of an optical element (resonant filter) used for a refractive index sensor of an embodiment of the present invention is shown in FIGS. 15A to 15E.

Figure 15A:
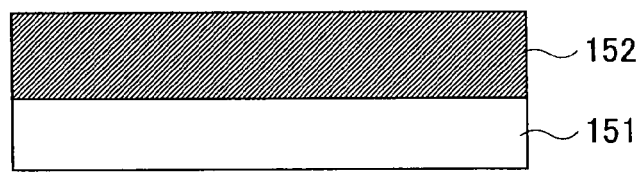
FIGS. 15A to 15E illustrate schematic diagrams showing a manufacturing method of an optical element (resonant filter) used in a refractive index sensor of the present invention.

First, a disc-shaped quartz glass substrate 151 is prepared, over which a $TiO_2$ thin film 152 (hereinafter also referred to as a $TiO_2$ layer) is formed by vacuum vapor deposition (FIG. 15A). The $TiO_2$ thin film 152 is configured to cause incident light to resonate. The $TiO_2$ film, in which a waveguide layer and a grating layer having protrusions and recessions are formed, is formed to have a total thickness of the waveguide layer and the grating layer. Here, a thin film with a high refractive index is required as the $TiO_2$ thin film 152. $Ta_2O_5$, $HfO_2$, and the like may be used instead of $TiO_2$ to obtain a thin film with a high refractive index.

Figure 15B:
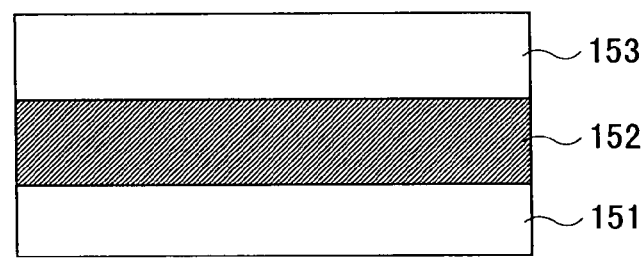

Subsequently, a structure with fine protrusions and recessions is formed on the $TiO_2$ layer 152. First, an i-line system positive type photoresist layer 153 is deposited on the $TiO_2$ thin film 152 by spin coating to have a thickness of about 80 nm (FIG. 15B). The photoresist layer 153 then undergoes a thermal process at about 100° C. by using a hot plate.

The fine pattern is formed on the photoresist layer 153. In the present invention, a structure having a periodic structure formed of protrusions and recessions with a constant pitch and a spatially changing fill factor is required to be formed as the fine pattern. Therefore, an Xθ type master disc exposure apparatus was used for forming the pattern of the structure. The Xθ type master disc exposure apparatus forms a spiral-shaped groove by translating a condensed exposure beam in a constant direction while rotating a master disc.

Figure 16:
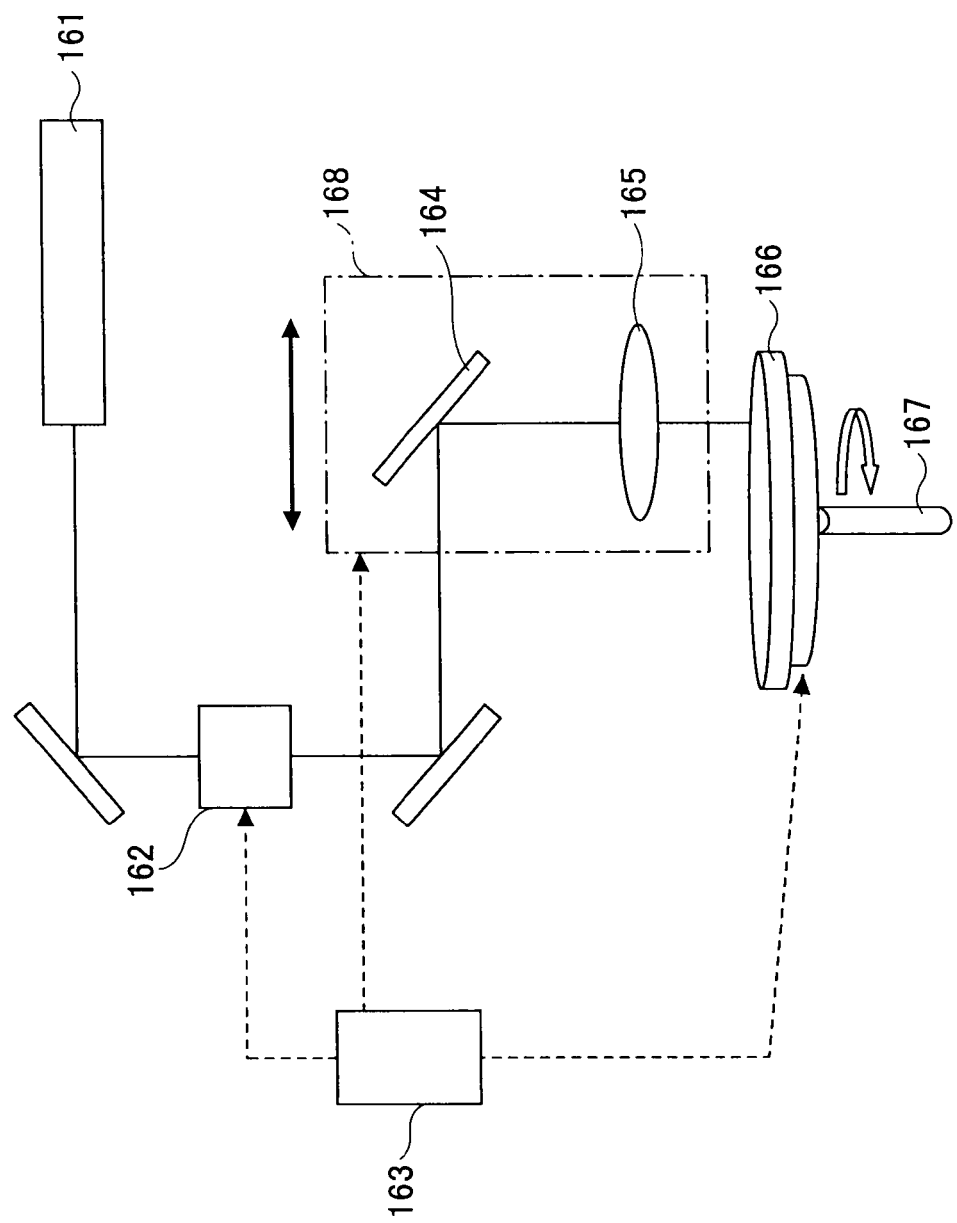
FIG. 16 illustrates a schematic diagram showing a configuration example of an exposure apparatus used for manufacturing an optical element (resonant filter) used in a refractive index sensor of the present invention.

The Xθ type master disc exposure apparatus is briefly described with reference to FIG. 16. A laser beam emitted by a light source 161 is modulated in light amount by a light modulator 162 and reflected by a mirror 164. The reflected laser light transmits through an objective lens 165 and is condensed on a surface of a substrate 166 to be exposed. The mirror 164 and the objective lens 165 are incorporated in an integrated translation unit 168 and controlled in position by an air slider.

The substrate 166 to be exposed here is mounted on a turn table on a spindle 167 and rotated in plane. A laser light source with a wavelength of 257 nm and the objective lens 165 with an NA (Numerical Aperture) of 0.9 were employed. The turn table was controlled in rotation speed by a radius so that an exposure linear speed becomes constant, and moved at a constant speed so that a pitch of the air slider becomes constant. The exposure linear speed was set at 3 m/sec. In the present invention, a fill factor can be changed by changing an amount of exposure on the substrate. Therefore, a controller 163 sends such signals to the light modulator 162 as to modulate an amount of light to be appropriate. The Xθ type master disc exposure apparatus is suitable for performing such an exposure as to change the fill factor, as in the present invention. Moreover, exposure can be performed at a higher speed than an XY scanning type exposure apparatus. By using such an apparatus, a structure width can be changed by finely changing an amount of exposure light. Therefore, a high-definition element in which a structure width minutely changes can be manufactured.

Figure 15C:
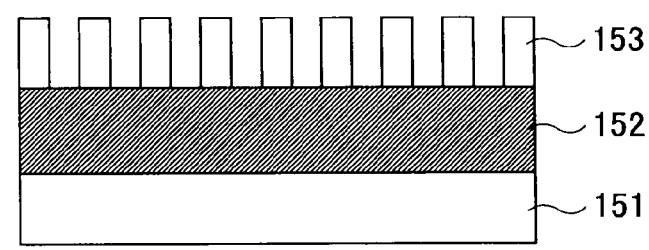

By using the Xθ type master disc exposure apparatus, a latent image is formed on the photoresist layer 153 by performing exposure with a pitch of 400 nm by changing an amount of light depending on positions. Through steps of developing, rinsing, and drying by shaking off, of the substrate, a structure having protrusions and recessions with a modulated fill factor is formed on the photoresist layer 153 (FIG. 15C).

Figure 15D:
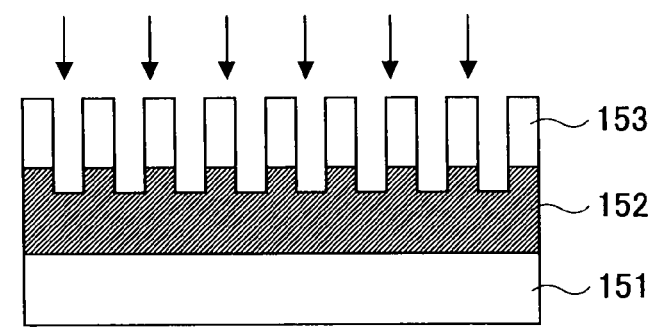
Figure 15E:
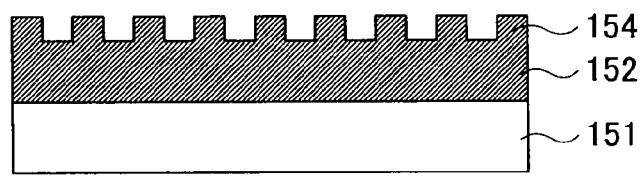

Subsequently, the $TiO_2$ layer 152 is etched by a predetermined depth by using the photoresist layer 153 having the protrusions and recessions as a mask (FIG. 15D). The etching is performed on the $TiO_2$ layer 152 by using a $CF_4$ gas. The photoresist layer 153 remaining after the etching is removed again by using an $O_2$ gas. In this embodiment, the $TiO_2$ layer 152 was etched by a depth of 30 nm. In this manner, the grating layer 154 is formed on the $TiO_2$ layer 152 (FIG. 15E).

In this embodiment, since the protrusions and recessions formed on the $TiO_2$ layer are shallow in depth, the etching can be formed by using the photoresist layer 153 as a mask. However, the etching can also be performed by using a metal pattern obtained by evaporating a metal thin film using the photoresist layer as a mask and removing the photoresist layer. Accordingly, a structure having a pitch of 400 nm, a structure width of 150 to 300 nm, a depth of the grating layer being 30 nm, and a thickness of the waveguide layer being 200 nm can be formed.

Here, the structure with spiral-shaped protrusions and recessions is formed with a fill factor modulated in the radial direction. However, since 1 mm is enough as a width to be used for an element, the formed protrusions and recessions are almost linear. By providing a photodetector with this resonant filter element, a highly sensitive refractive index sensor can be formed.

Here, the Xθ type master disc exposure apparatus was used for manufacturing the resonant filter, but the resonant filter can also be manufactured by an XY type exposure apparatus and the like.

In the above embodiments, the optical element of the present invention is used as the resonant filter, and the refractive index sensor, the refractive index sensor array, and the biosensor formed by combining the resonant filter and a photodetector have been described. The optical element of the present invention can be used as an optical filter which transmits light having a specific wavelength. Moreover, the optical element of the present invention can also be applied to a polarizing sensor for detecting a polarizing direction of light, and to various optical devices.

An optical element of one embodiment of the present invention has a structure in which a structure width of a periodic structure is spatially changed (more specifically, a structure in which a structure width of a periodic structure is spatially changed with a constant period, or a structure in which a structure width of a periodic structure is spatially changed with a constant refractive index). Accordingly, an optical element which causes light with a specific wavelength to resonate and be reflected can be provided by utilizing resonant reflection caused by a periodic structure formed of fine protrusions and recessions in a size equal to or less than a wavelength of incident light.

Further, according to one embodiment, the optical element of the present invention can be used as a resonant filter that can cause incident light having a specific wavelength to resonate and be reflected by utilizing the resonance between the incident light and a periodic structure having fine protrusions and recessions in a size equal to or less than a wavelength of the incident light, and an optical filter that can transmit light having a specific wavelength by utilizing the resonance between the incident light and a periodic structure having fine protrusions and recessions in a size equal to or less than a wavelength of the incident light.

According to one embodiment, a refractive index sensor which includes a photodetector using the above-described optical element to detect transmitted light or reflected light and thus is capable of detecting a refractive index of a part (measurement sample) around the protrusions and recessions according to a position where incident light resonates and is reflected can be provided.

Accordingly, a spectroscope which has normally been required to detect a change in the refractive index is not required, and a change in the refractive index of a measurement sample can be detected as a change of a position where resonant reflection occurs. Moreover, since a change in a resonant wavelength that corresponds to a change of a fill factor is quite small, a considerably high resolution is achieved with respect to the change of the refractive index. Therefore, a minute change in the refractive index can be detected at a high precision. Accordingly, a change of a vital reaction, which has conventionally been difficult to detect, can be detected with high sensitivity.

The refractive index sensor of an embodiment of the present invention has a structure in which the photodetector is formed of plural light receiving elements which are arranged in an array in accordance with the changes of a structure width of a periodic structure of the optical element, a structure in which the photodetector is formed of a linear CCD which is set in accordance with a change of a structure width of a periodic structure of the optical element, or a structure in which the photodetector is formed of a linear CMOS sensor which is set in accordance with a change of a structure width of a periodic structure of the optical element. In this manner, when the photodetector is formed in an array in accordance with a change of the fill factor, a change in the refractive index can be detected stably in real time without using a movable part.

Further, according to one embodiment of the present invention, the optical element and the photodetector are stacked on each other in series with respect to an incident direction of light. Accordingly, a thickness of a sensor part can be considerably reduced, and at the same time it becomes quite easy to adjust positions of the optical element and the photodetector. As a result, a simple refractive index sensor can be formed.

The refractive index sensor array of an embodiment of the present invention is formed by arranging the above-described refractive index sensor in a one-dimensional or two-dimensional array. Accordingly, by fixing different DNAs or proteins to each of the refractive index sensors arranged in the array, plural reaction tests can be performed at the same time without using a label such as a fluorescence substance. Therefore, by using this refractive index sensor array, a biosensor that checks antibody reactivity and the like can be provided.

This patent application is based on Japanese Priority Patent Application No. 2008-186773 filed on Jul. 18, 2008, the entire contents of which are hereby incorporated herein by reference.

What is claimed is:

1. An optical element for resonating and reflecting incident light having a wavelength, comprising:
   a periodic structure formed of protrusions and recessions, a period of the periodic structure being equal to or less than the wavelength of the incident light, and the incident light having the wavelength being resonated and reflected by a resonance caused between the incident light and the protrusions and recessions,
   wherein widths of the protrusions are spatially changed.

2. The optical element as claimed in claim 1, wherein the widths of the protrusions are spatially changed while the period of the periodic structure is set constant.

3. The optical element as claimed in claim 1, wherein the widths of the protrusions are spatially changed while a refraction index of the periodic structure is set constant.

4. A refractive index sensor comprising:
   an optical element for resonating and reflecting incident light having a wavelength, the optical element including a periodic structure formed of protrusions and recessions, a period of the periodic structure being equal to or less than the wavelength of the incident light, and the incident light having the wavelength being resonated and reflected by a resonance caused between the incident light and the protrusions and recessions, and widths of the protrusions being spatially changed;
   a photodetector configured to detect a position on the optical element where the incident light is reflected,
   wherein the position on the optical element changes in accordance with a refractive index of a sample provided on the optical element.

5. The refractive index sensor as claimed in claim 4, wherein the photodetector is formed of plural light receiving elements, and the light receiving elements are arranged in an array according to a change in the widths of the protrusions of the periodic structure of the optical element.

6. The refractive index sensor as claimed in claim 4, wherein the photodetector is formed of a linear CCD; and the linear CCD is provided according to a change in the widths of the protrusions of the optical element.

7. The refractive index sensor as claimed in claim 4, wherein the photodetector is formed of a linear CMOS sensor; and the linear CMOS sensor is provided according to a change in the widths of the protrusions of the optical element.

8. The refractive index sensor as claimed in claim 4, wherein the optical element and the photodetector are stacked on each other.

9. A refractive index sensor array comprising:
   a refractive index sensor including
      an optical element for resonating and reflecting incident light having a wavelength, the optical element including a periodic structure formed of protrusions and recessions, a period of the periodic structure being equal to or less than the wavelength of the incident light, the incident light having the wavelength being resonated and reflected by a resonance caused between the incident light and the protrusions and recessions, and widths of the protrusions being spatially changed, and a photodetector configured to detect a position on the optical element where the incident light is reflected, the position on the optical element changing in accordance with a refractive index of a sample provided on the optical element, wherein the refractive index sensor is arranged in a one-dimensional or two-dimensional array.

10. A biosensor comprising the refractive index sensor array as claimed in claim 9.

11. The optical element as claimed in claim 1, wherein the periodic structure includes a material that is transparent with respect to the incident light.

* * * * *